United States Patent [19]
Vénica et al.

[11] Patent Number: 6,091,484
[45] Date of Patent: Jul. 18, 2000

[54] OIL QUANTITY AND QUALITY INDICATOR

[75] Inventors: Néstor Juan Vénica; Rafael Antonio Colussi, both of Provincia de Santa Fe, Argentina

[73] Assignee: Col-Ven S.A., Provincia de Santa Fe, Argentina

[21] Appl. No.: 08/862,679

[22] Filed: May 23, 1997

[51] Int. Cl.[7] .................................................. G01N 33/28
[52] U.S. Cl. .................................... 356/70; 356/301
[58] Field of Search ................................. 356/70; 250/301

[56] References Cited

U.S. PATENT DOCUMENTS

| | | | |
|---|---|---|---|
| 3,417,250 | 12/1968 | Kadivnik .................................... | 356/70 |
| 3,892,485 | 7/1975 | Merritt et al. ............................. | 356/70 |
| 5,076,397 | 12/1991 | Yamada ...................................... | 356/70 |
| 5,194,910 | 3/1993 | Kirkpatrick, Jr. et al. ............... | 356/70 |
| 5,196,898 | 3/1993 | Tamura et al. ............................. | 356/70 |
| 5,296,843 | 3/1994 | Wohlstein et al. ........................ | 356/70 |
| 5,691,701 | 11/1997 | Wohlstein et al. ........................ | 356/70 |

*Primary Examiner*—Robert H. Kim
*Attorney, Agent, or Firm*—McDermott, Will & Emery

[57] ABSTRACT

Method for monitoring oil state which combines optical transmissivity of oil with certain kinds of optoelectrical optodetector. In particular, the oil state in automatic gearboxes is monitored to detect lack of oil quantity or quality and, furthermore, to detect malfunction of gearbox mechanisms. A region of the oil is scanned with infrared oil and the amount of light reaching straight accross a short gap in said region is detected to derive monitoring information.

13 Claims, 2 Drawing Sheets

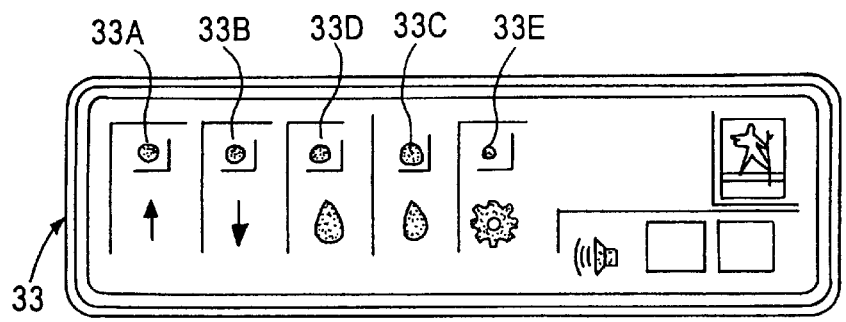
FIG. 3
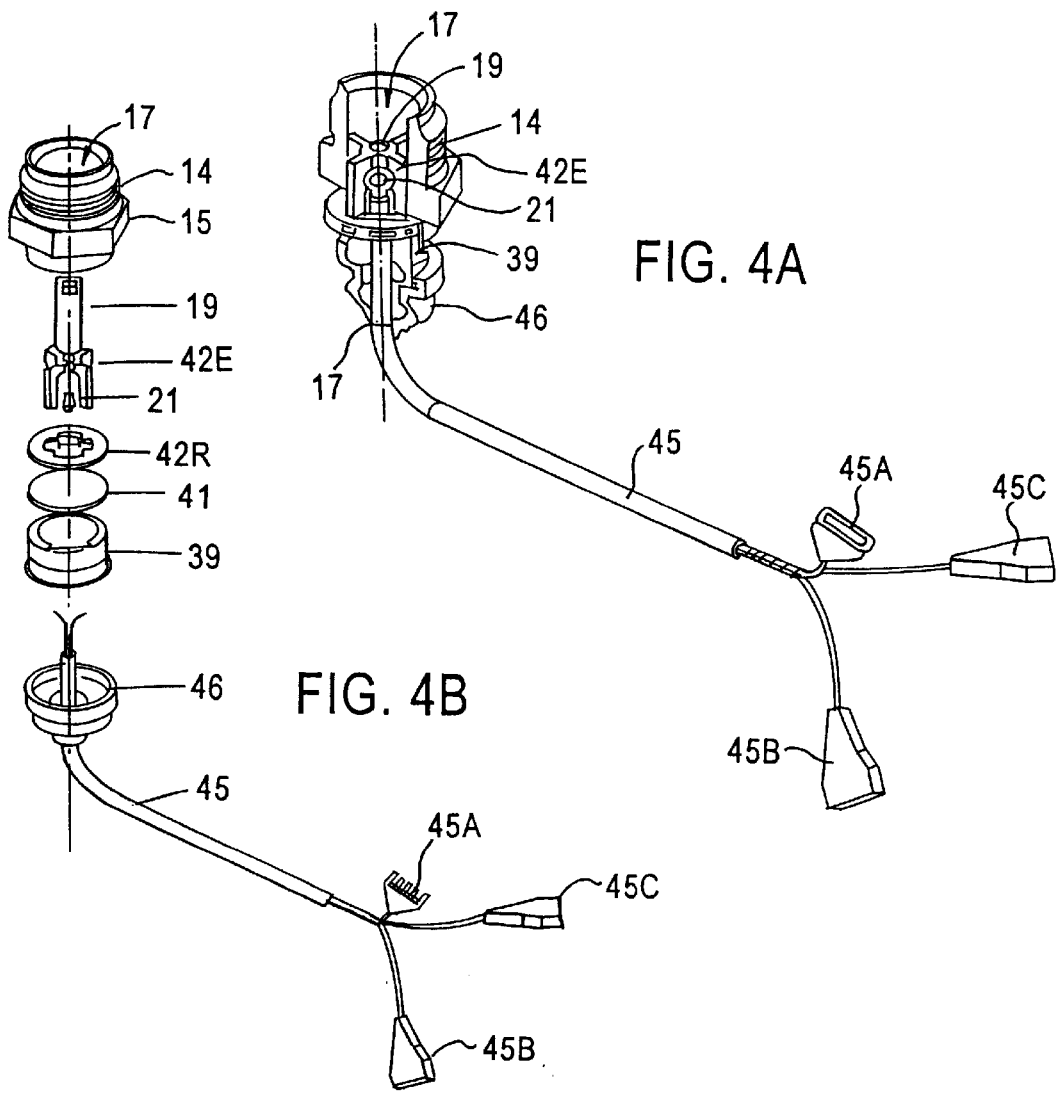
FIG. 4A
FIG. 4B

OIL QUANTITY AND QUALITY INDICATOR

FIELD OF THE INVENTION

The present invention is generally related to lubricated machines, engines and mechanisms and, in particular, to the quantity and/or quality of lubricant present for protecting such mecanisms. More particularly, the present invention concerns obtaining an indication of the lubricant state, specially when it is inadequate.

The invention finds particular application, but not exclusively, to protecting automatic gearboxes in motor-vehicles, such as busses, lorries and road machinery, for example. Such gearboxes have rather delicate mechanisms in that the oil level therein should be in between predetermined levels and of good quality for lubricating the mechanisms properly.

Oil levels either too low or too high are harmful, as the oil is beated with small air bubbles in suspension. Furthermore, oil gradually becomes contaminated during its useful life by small particles worn off lubricated mechanism parts and ages from different factors, particularly from hot temperatures.

The invention also presents other applications for detecting abnormalities in the operation of automatic gearboxes, such as sucking air in through deteriorated seals, piping losses or filter obstructions or when the converter traction disks slip for some reason or other such as low pressure, overload, air in the oil, internal losses because of worn parts, etc.

SUMMARY OF THE INVENTION

The present invention arises from the discovery that the state of the oil may be detected precisely in view of that the translucidness of the oil (i.e. the light transmissivity) diminishes as the lubricant quality degrades. When the oil is beated in the presence of bubbles, the interphases where the refraction index changes reflect and refract light, such that the light waves depart from their natural straight-line path, the oil taking on a milky colour. Moreover, oil gets darker when it ages or gets contaminated, which also has the effect of reducing the optical transmissivity thereof. Therefore, by virtue of these phenomena, bad state of the oil from either or both aging of the oil itself or malfunction of an automatic gearbox, such as traction disk slippage, may be detected from the light transmissivity of oil to prevent damage to lubricated mechanical parts.

In accordance with the above, the invention comprises a method for monitoring the state of oil or other viscous fluid in a container, such as the carter of an automatic gearbox, comprising the steps of scanning a region of the fluid with light of a certain strength, detecting the strength of the light that traverses the fluid to a predetermined distance from where it was scanned and deriving the state of the fluid from the magnitude of the detected light strength relative to a predetermined scale of magnitudes. The scale comprises a normal range of detected light magnitudes corresponding to the fluid in adequate quantity and quality and another range representative of oil in a degraded state wherein the light is obstructed or the fluid is less translucid and, hence, of lesser magnitudes than the first interval.

The present invention also encompasses an oil-state indicator-device which includes an optoelectronic assembly submergible in the fluid and comprising a light-emitting element and; comprising a light-emitter element y a light-sensor element. The sensor element is placed a predetermined distance opposite the light emitter and connected to a strength encoder circuit, the output of which is indicative of to which of the lubricant normal or abnormal states the detected strength corresponds. The output from the encoder circuit is connected to an indicator element advantageously installed on the dashboard of a vehicle or a machine, to provide an alarm signal to the driver thereof whenever the oil state is substandard.

The optoelectronic assembly may comprise a support with a hollow inside which is communicated to the outside of the support by a passage for the lubricant to pass through. The support may be fitted to a threaded hole in the lubricant container, such as one or two normally-closed holes provided by gearbox manufacturers, such as one provided for example for upper inspection of the gearbox carter and which is at a predetermined minimum lubricant level. Directing and detecting light at this level enables determining when there is not enough oil for operation of the gearbox in addition to the quality thereof.

We have found that excellent results are obtained by using a phototransisistor as the sensor element since a substantial signal amplitude variation may be had in the signal output for the different lubricant states to be detected by means of adequate selections of the emitter current and of the gap between the emitter and sensor pair of elements. Preferibly, a second optoelectronic assembly may be added for detecting excessively high fluid levels and providing a binary output.

The indicator element is preferibly integrated in a dashboard unit which also houses the encoder circuit and an electric power supply. The unit may comprise an array of colour-coded light-emitter diodes (LED) on a unit front panel in addition to a sound alarm which may be controlled to ring when an abnormal-state indicator diode is lit.

BRIEF DESCRIPTION OF THE DRAWINGS

These and other features and details of the subject matter of the invention and how it may be put to practice may be understood better from the ensuing detailed description of a preferred embodiment taken in connection with the accompanying drawings, wherein:

FIG. 3 shows the front of the indicator panel installed in the dashboard, on a unit which houses the circuit of FIG. 2, to provide a visual indication of the qualitative and quantitative state of the oil in the carter of FIG. 1.

FIG. 4A illustrates, in greater detail and partly cut away, one of the two identical opto-electronic assemblies of FIG. 1, which FIG. 4B shows in disassembled form.

THE PREFERRED EMBODIMENT OF THE INVENTION

Figure 1:
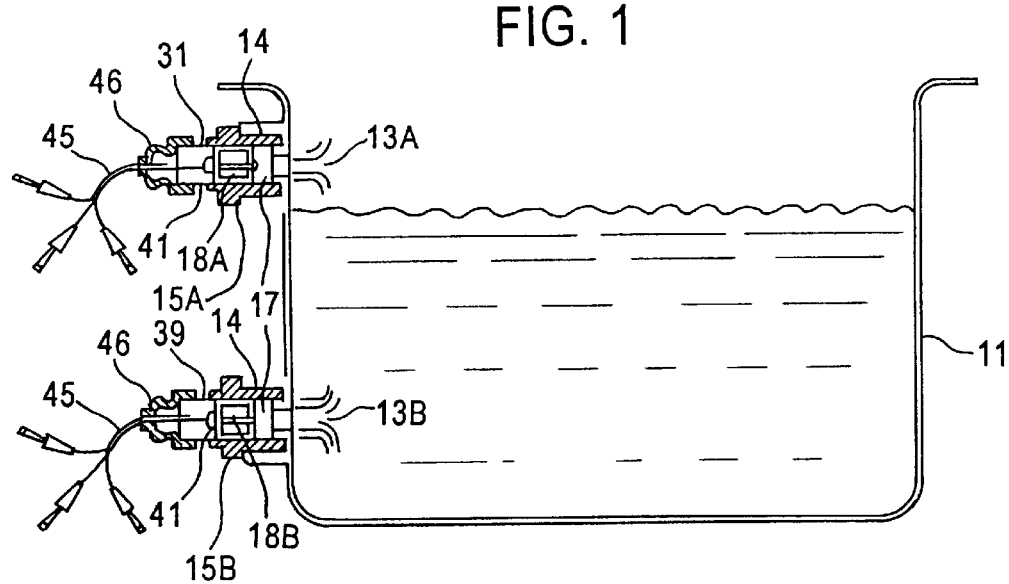
FIG. 1 schematically illustrates a cross section of a carter for holding lubricator oil, wherein two optoelectronic assemblies have been installed at the minimum and maximum permissible levels, according to a preferred embodiment of the invention.

FIG. 1 illustrates a carter 11 for holding oil A for lubricating an automatic gearbox (not illustrated). The carter 11 is convenetionally manufactured with two holes 13A and 13B which are threaded 14 and normally covered, provided ideally for visually inspecting the maximum and minimum oil levels respectively.

According to the present invention, a support 15B is screwed into the minimum-level hole 13B. An optoelectronic assembly 18B is housed in the inside 17 of the support 15B. The optoelectronic assembly 18B is formed by a light-emitter element 19B, such as an infrared diode, and a photosensor element 21B, preferibly embodied by a phototransistor, although other optoelectronic elements may be eventually used. It is important that the phototransistor 21B be installed opposite the emitter 19B, so that infrared light may impinge thereon directly from the latter, and that the gap in between both photoelements 19B and 21B, on which the selected emitter bias current depends, be such that a suitable excursion is obtained along the substantially linear portion of the response of the phototransistor 21B in the active state along the full range of oil states to be detected. These states correspond to:

Maximum impinging light: corresponding to air filling the gap between the pair of photoelements 19B–21B, in view of that air, being transparent, is substantially more translucid than whatever oil is used for lubricating the gearbox. That is, this state represents no oil A at this level, i.e. not enough oil in the carter 11.

Intermediate range of magnitudes: corresponds to sufficient oil A and in good state (maximum translucidness of the non-transparente fluid).

Minimum range of magnitudes: the colour of the oil A is dark or milky, meaning that the quality thereof is deficient for some reason. The light output by the emitter 19B is absorbed by the dark oil A or else is reflected and refracted at the interphases formed by the air bubbles present therein, thereby blocking light from reaching the phototransistor 21B to some degree. The detected strength magnitude is dependent on the degree of degradation of the fluid A.

Figure 2:
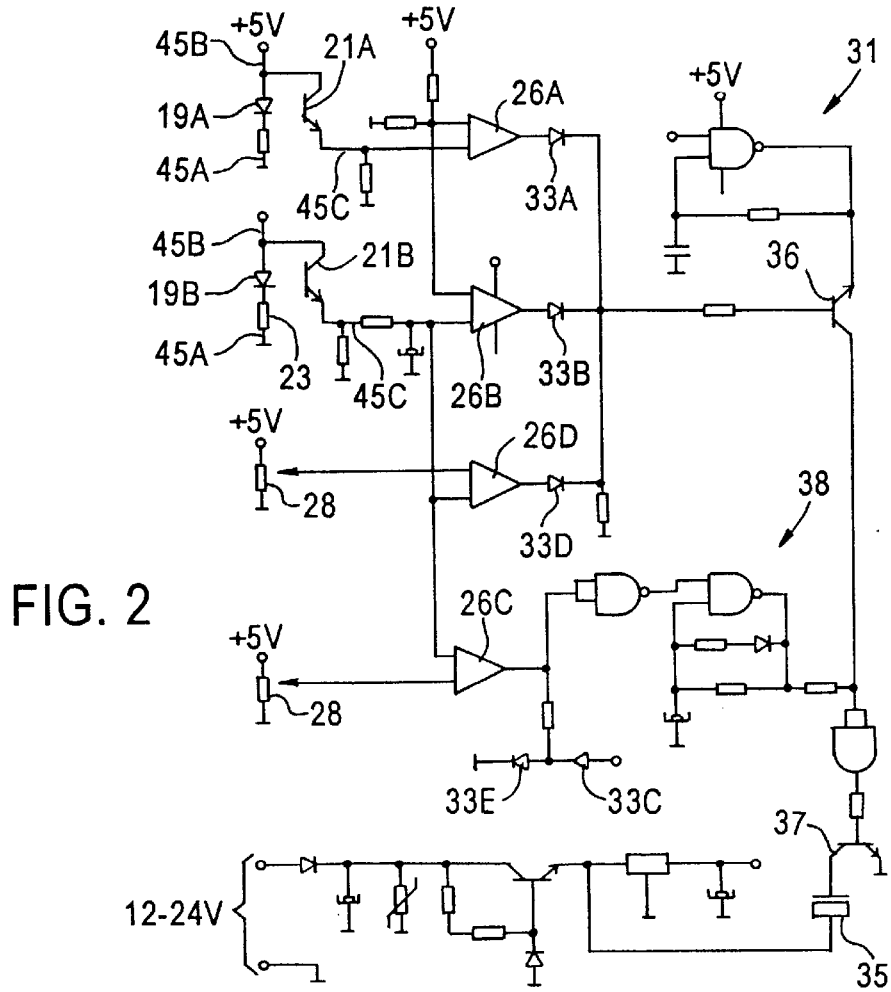
FIG. 2 is a circuit schematic of the electronic encoder which forms another part of the indicator device of the invention, physically remote from the optoelectronic assembly of FIGS. 4A and 4B.

The optoelectronic assembly 19B–21B is biased so that the phototransistor 21B operates along the most linear part of its curve. This makes calibration simpler, The electronic circuit set forth in FIG. 2 is powered by a 5 volt regulated supply that drives the LED 19B at a predetermined constant current according to the selection of a limitter resistor 23.

The preferred embodiment of the invention further suggests signalling an excessive oil level, harmful to some mechanisms, referring back to FIG. 1, a support 15A housing a second optoelectronic assembly 18A is fitted into the maximum-level hole 13A in the carter sidewall. The additional optoelectronic assembly 18A comprises a second infrared diode 19A and a second phototransistor 21A, designed to be identical in composition and construction to the first assembly 18B, although it is adapted to operate differently since the phototransistor 21A is set to operate as a binary switch. The infrared diode 19A of this assembly 18A is driven in the same manner as the diode 19B of the other assembly 18B. The associated phototransistor 21A is connected to the inverter input of a comparator amplifier 26A, the output of which controls a red light-emitting diode (LED) 33A installed on dashboard, as described more fully hereinafter. In this way, the phototransistor 21A is cut off and drives the amplifier 26A to turn an alarm light 33A on when the oil level in the carter 11 is over the maximum permissible level. Otherwise, the transistor 21A is saturated and the LED 33A turned off when the level is lower such that there is no oil in between the emitter 19A and the sensor 21A.

On the other hand, a level of oil A too low in the carter 11, because of some loss, means no lubricant fluid A in the gap in between both photoelements 19B–21B such that maximum light strength impinges on the phototransistor 21B. The photo-transistor 21B operates the other way round in relation to the other, saturating when the oil level is not enough, which is why it is connected to the non-inverter input of a comparator amplifier 26B, the output of which controls a red light-emitting diode (LED) 33B mounted to the dashboard, as described more fully hereinafter. In this way, the phototransistor 21B saturates under lack of oil at the minimum level of the carter 11, causing the amplifier 26B to switch a second alarm light 33B. Otherwise, when the oil level is over the minimum permissible oil level, oil A is present in between the emitter 19B and the sensor 21B. The transistor 21B thereby conducts and generates a signal the amplitude of which represents the qualitative state of the liquid A, but which is strong enough anyway for the amplifier 26B to keep the alarm LED 33B unlit.

Both amplifieres 26A y 26B, together with two other similar comparator amplifiers 26C and 26D are integrated on a single integrated-circuit chip 26 and make up a voltage signal encoder circuit 29. The amplifiers 26C and 26D each have one of their inputs connected to the output of the phototransistor 21B, while the remaining input is connected to a respective preset 28 which is adjusted to define switching points between the different lubricant states.

When the oil A begins to loose translucidness when it starts to get contaminated or beaten, in the latter case because of excessive oil or because of air intake through a blocked filter or a faulty gasket, or to darken because of malfunction of a lubricated mechanism, for example when the gearbox converter traction disks start slipping. When the oil mixes with air, the small air bubbles in the oil refract the light, portraying a milky colour. In either case, the output of the phototransistor 21B falls and thereby activates the amplifier 26C to light up a corresponding yellow LED 33C, to alert the driver.

By the time the state of the oil A gets even worse, the fluid A is hardly translucid or practically not at all so that little or no light impinges on the phototransistor 21B. The amplifier 26D activates its output to light up a third red LED 33D in the dashboard indicator. A lit red light 33D informs the driver that he should stop immediately, since the oil has degraded completely or the state thereof, which may be transitory, is not good enough for a minimum recommended lubrication, thereby risking damage to the gearbox if it continues operating.

In the normal state, the output of amplifier 26C will be high to turn on a corresponding green indicator LED 33E on the dashboard of the vehicle, indicating good (normal) state of the oil A both in quantity and in quality. This green LED 33E turns off when the yellow LED 33C turns on, indicating that the oil quality is in an intermediate state.

The alert and alarm signals are preferibly backed up by a buzzer 35 activated by a fast oscilator circuit 34. At the same time any one of the red LEDs 33A, 33B or 33D is lit, indicating major danger, a transistor switch 36, the base of which is controlled by the higher level of the outputs of the amplifiers 26A, 26B or 26D is closed, to turn on a power transistor 37 which sounds the buzzer 35 continuously intermittently. On the other hand, if the yellow LED 33C lights up, when the danger is minor, the amplifier 26C activates an asymetrical oscillator 38 which sounds the buzzer 35 every 40 seconds.

FIG. 3 shows an array 33 of indicator LEDs on the instrument dashboard. As previously described, the array 33 comprises five lamp indicators, that is end LED 33A indicating too much oil A, followed by LED 33B, also red, indicative of lack of oil A, and then the LEDs 33D and 33C, which are respectively red and yellow, indicative of deficient oil quality, followed lastly by the green LED 33E at the other end indicative of good oil stat.

FIGS. 4A and 4B represent a preferred embodiment of the support 15 and the optoelectronic pair 19-21 corresponding to any one of the like assemblies 18. The assembly 18 comprises a sleeve 15 closed at one end by a protector cap 39. The sleeve houses respective support guides 42E and 42R in its hollow inside 17 to mount the corresponding emitter 19 and sensor 21 elements opposite one another and separated by the required gap, which is about 1 cm (around ⅜"). The inside 17 of the support 15 fills with oil A through the hole 13 and bathes the supports 42 and the optoelectronic assembly 19-21. The leads of the optoelectronic elements 19 are 21 electrically connected to a printed circuit 41 housed in the cap 39 which closes off the outside end of the sleeve 15.

The electronic circuit 29 and the indicator array 33 of FIGS. 2 and 3 form an assembly which is installed on the vehicle dashboard and which is connected to the assembly 15 of FIG. 4 by electrical conductors 45 extending between the carter 11 and the dashboard. As shown in each of FIGS. 4, there are three leads 45 connected to the board 41 and which emerge from the support 15 through a hermetic hole 47 in the end of the gap 39 through a dust cover 46. One lead 45A is connected to ground, another lead 45B to the battery of the vehicle via the regulated power supply and the third lead 45C connects the phototransistor 21 to the input of one or more amplifiers 26 in the dashboard.

Of course, changes, variations and aggregations may be applied to the above-detailed embodiment, without departing from the scope nor the spirit of the invention. The same has been described by way of a preferred embodiment, however those skilled in the art may suit it to other applications without departing from the purview of the invention as set forth in the appended claims. For example, visible light instead of infrared light could be used to scan the oil A in the carter 11.

We claim:

1. A method for monitoring the state of a liquid lubricant, said method comprising the steps of:
    scanning a region of the lubricant with light of a certain strength;
    detecting the amount of light that traverses said lubricant in said region and reaches a predetermined distance from where it was scanned, and
    deriving the state of the lubricant from the amount of detected light relative to a range of predetermined strength magnitudes, wherein said deriving step includes deriving an alarm state of lubricant upon said detecting step detecting either a substantially maximum or a substantially minimum strength of light at a predetermined minimum level of said lubricant.

2. A method according to claim 1, wherein said light comprises infrared light.

3. A method according to claim 1 wherein said deriving step includes deriving that said lubricant is mixed or beaten with air to a degree determined from the strength of the detected light.

4. A method according to claim 1, wherein said deriving step includes deriving an alarm state of excess lubricant upon said detecting step detecting a level of light below a certain threshold at a predetermined maximum level of said lubricant.

5. A method according to claim 1, for detecting malfunction of mechanisms lubricated by said lubricant in a automatic gearbox in a vehicle by a step of detecting a low optical transmissivity of said lubricant.

6. A method according to claim 5, in an automatic gearbox including a converter traction mechanism, wherein said step of detecting said low optical transmissivity of said lubricant is used to detect that the converter traction mechanism is not operating properly.

7. A device for mounting to a lubricant container in a motor-vehicle for indicating the state of a lubricant therein, said device comprising:
    an optoelectronic assembly adapted for immersion in a region of the lubricant, said optoelectronic assembly comprising a light emitter element and a light sensor element spaced substantially opposite from said emitter to form a gap of a predetermined distance between said light emitter and sensor elements, whereby said sensor means comprises a phototransistor element to receive light from said emitter means across said gap and generate an output signal indicative of the amount of light received;
    circuit means for comparing said sensor output signal and encoding an indicator signal indicative of the amount of light received and thereby indicative of the lubricant state; wherein said circuit means includes comparator circuits for encoding said indicator signal in at least three non-overlapping ranges of optical transmissivity in said lubricant, said non-overlapping ranges including a high end range substantially corresponding to optical transmissivity in air, a low end range corresponding to optical transmissivity in oil in bad state and an intermediate range corresponding to optical transmissivity in oil in good state; and
    indicator means responsive to said comparator circuits for receiving said encoded signal and providing an indication of said lubricant state, said state indication including at least one alarm state corresponding to said two end ranges.

8. A device according to claim 7, wherein said optoelectronic assembly comprises a support having a hollow inside communicated through a passage to the outside of said support and wherein both said emitter and sensor elements are housed inside said hollow inside to be exposed to said lubricant entering through said passage and thereby varying the optical transmissivity in said gap.

9. A device according to claim 8, wherein said support comprises a sleeve comprising an open end for passage of said lubricant and a closed end opposite said open end and having a seal for preventing passage of said lubricant, said assembly further including electrical conductors extending through said seal for connecting said sensor element to said circuit means.

10. A device according to claim 9, wherein said sleeve includes an external thread formed thereon for mounting said support to said lubricant container at a level corresponding to a predetermined minimum lubricant level.

11. A device according to claim 7, further comprising an additional optoelectronic assembly adapted for immersion in a region of the lubricant at a level higher than the first optoelectronic assembly corresponding to a predetermined maximum level, wherein said additional optoelectronic assembly is constructively similar to said first optoelectronic assembly and includes a second phototransistor element connected to said circuit means for said circuit means to signal an indication of excess lubricant upon said second phototransistor element providing an indication that optical transmissivity of said lubricant is reduced at said higher level.

12. A device according to claim 7 wherein said comparator circuits are further coupled to audible alarm means to be activated simultaneously with at least one of two end ones of said three nonoverlapping ranges of transmissivity.

13. A device according to claim 7, wherein said gap is about 1 cm.

* * * * *